(12) United States Patent
Kaushal et al.

(10) Patent No.: US 8,523,785 B2
(45) Date of Patent: *Sep. 3, 2013

(54) METHOD AND APPARATUS FOR MEASURING ANALYTES

(75) Inventors: Ash Kaushal, Mississauga (CA); Duncan MacIntyre, Campbellville (CA)

(73) Assignee: Covidien LP, Mansfield, MA (US)

( * ) Notice: Subject to any disclaimer, the term of this patent is extended or adjusted under 35 U.S.C. 154(b) by 1255 days.

This patent is subject to a terminal disclaimer.

(21) Appl. No.: 12/066,072

(22) PCT Filed: Aug. 24, 2006

(86) PCT No.: PCT/CA2006/001391
§ 371 (c)(1),
(2), (4) Date: Jun. 11, 2008

(87) PCT Pub. No.: WO2007/028233
PCT Pub. Date: Mar. 15, 2007

(65) Prior Publication Data
US 2009/0168049 A1  Jul. 2, 2009

Related U.S. Application Data

(60) Provisional application No. 60/714,476, filed on Sep. 6, 2005.

(51) Int. Cl.
*A61B 5/00* (2006.01)

(52) U.S. Cl.
USPC .......................................... 600/583; 356/319

(58) Field of Classification Search
USPC ................................ 600/583, 573; 422/82.05
See application file for complete search history.

(56) References Cited

U.S. PATENT DOCUMENTS

| | | | |
|---|---|---|---|
| 4,387,972 A | 6/1983 | Valencia | |
| 4,637,403 A | 1/1987 | Garcia et al. | |
| 4,791,938 A | 12/1988 | Van Valkenburg | |
| 5,207,984 A | 5/1993 | Kheiri | |
| 5,361,758 A | 11/1994 | Hall et al. | |
| 5,522,388 A | 6/1996 | Ishikawa et al. | |
| 5,736,103 A | 4/1998 | Pugh | |
| 5,796,476 A * | 8/1998 | Wang et al. | 356/301 |

(Continued)

FOREIGN PATENT DOCUMENTS

| | | |
|---|---|---|
| CA | 2475622 A1 | 1/2005 |
| WO | WO 98/39634 | 9/1998 |
| WO | WO 99/47261 | 9/1999 |
| WO | WO 00/70350 | 11/2000 |
| WO | WO2006081380 A3 | 8/2006 |

OTHER PUBLICATIONS

U.S. Appl. No. 11/463,232; Inventor: MacIntyre et al.; Office Action dated Jan. 9, 2009.

(Continued)

*Primary Examiner* — Max Hindenburg
*Assistant Examiner* — Renee Danega
(74) *Attorney, Agent, or Firm* — Hovey Williams LLP

(57) ABSTRACT

A method for measuring the concentration of a compound in the blood of a part of a subject is provided. An invasive or non-invasive sample of blood may be used for this determination. Also provided is a device for measuring the concentration of a compound in the blood of a subject. The device comprises a source of electromagnetic radiation, a holder, a detector and a processing system.

12 Claims, 6 Drawing Sheets

(56) References Cited

U.S. PATENT DOCUMENTS

| | | | |
|---|---|---|---|
| 5,800,781 | A | 9/1998 | Gavin et al. |
| 5,912,179 | A | 6/1999 | Alvarez et al. |
| 6,040,578 | A | 3/2000 | Malin et al. |
| 6,099,484 | A | 8/2000 | Douglas et al. |
| 6,236,047 | B1 | 5/2001 | Malin et al. |
| 6,353,471 | B1 | 3/2002 | Samsoondar et al. |
| 6,365,363 | B1 | 4/2002 | Parfenov et al. |
| 6,430,513 | B1 | 8/2002 | Wang et al. |
| 6,526,298 | B1 | 2/2003 | Khalil et al. |
| 6,651,015 | B2 | 11/2003 | Samsoondar |
| 6,741,876 | B1 | 5/2004 | Sceciena et al. |
| 6,819,950 | B2 | 11/2004 | Mills |
| 6,849,052 | B2 * | 2/2005 | Uchigaki et al. ............... 600/584 |
| 7,016,021 | B2 | 3/2006 | Nakajima et al. |
| 7,050,157 | B2 | 5/2006 | Braig et al. |
| 7,194,369 | B2 | 3/2007 | Lundstedt et al. |
| 7,343,185 | B2 | 3/2008 | Samsoondar et al. |
| 7,377,794 | B2 * | 5/2008 | Al-Ali et al. .................... 439/77 |
| 7,524,671 | B2 * | 4/2009 | Clarke et al. ............... 435/287.1 |
| 2003/0086073 | A1 | 5/2003 | Braig et al. |
| 2003/0204133 | A1 | 10/2003 | Harjunmaa et al. |
| 2004/0073120 | A1 | 4/2004 | Motz et al. |
| 2004/0260204 | A1 * | 12/2004 | Boecker et al. ............... 600/584 |
| 2005/0019936 | A1 * | 1/2005 | Samsoondar et al. .......... 436/80 |
| 2005/0036147 | A1 | 2/2005 | Sterling et al. |
| 2005/0250212 | A1 * | 11/2005 | Azizian ........................... 436/71 |
| 2006/0167382 | A1 | 7/2006 | Deshmukh |
| 2007/0110621 | A1 | 5/2007 | MacIntyre |
| 2009/0221886 | A1 | 9/2009 | Kaushal et al. |

OTHER PUBLICATIONS

Extended European Search Report dated Jul. 13, 2009 re NIR Diagnostics, Inc. Application No. 06775090.1-2319 / 1928314 PCT/CA2006001310 (9 pgs).

Extended European Search Report dated Jul. 28, 2009 re NIR Diagnostics, Inc. Application No. 06790572.9-2319 / 1931257 PCT/CA2006001391 (10 pgs).

Article—Journal of Cosmetic Science, 54, 119-131 (Mar./Apr. 2003) titled Penetration Studies of Vitamin E Acetate Applied from Cosmetic Formulations to the Stratum Corneum of an In Vitro Model Using Quantification by Tape Stripping, UV Spectroscopy, and HPLC.

Article—Journal of Controlled Release, 12 (1990) 67-75; Elsevier Science Publishers B.V., Amsterdam—Printed in The Netherlands entitled Oleic Acid Concentration and Effect in Human Stratum Corneum: Non-Invasive Determination by Attenuated Total Reflectance Infrared Spectroscopy In Vivo.

Office Action dated Jun. 8, 2010 re U.S. Appl. No. 11/463,232, filed Aug. 8, 2006; Inventor: MacIntrye, Duncan (8 pages).

Advisory Action issued Oct. 1, 2012 on U.S. Appl. No. 11/463,232.

Office Action issued Dec. 4, 2012 on European Patent Application No. 06775090.1.

Office Action issued Apr. 19, 2013 on U.S. Appl. No. 12/066,065.

Office Action issued Apr. 22, 2013 on U.S. Appl. No. 11/463,232.

Office Action dated Sep. 24, 2009 issued on U.S. Appl. No. 11/463,232.

Office Action dated Nov. 18, 2010 issued on EP 06775090.1.

Office Action dated Dec. 8, 2010 issued on U.S. Appl. No. 11/463,232.

Office Action dated Mar. 24, 2011 issued on U.S. Appl. No. 11/463,232.

Office Action dated Jun. 8, 2011 issued on U.S. Appl. No. 12/066,065.

Office Action dated Aug. 22, 2011 issued on U.S. Appl. No. 11/463,232.

Final Rejection dated Nov. 21, 2011 issued on U.S. Appl. No. 12/066,065.

Office Action dated Feb. 27, 2012 issued on U.S. Appl. No. 11/463,232.

* cited by examiner

METHOD AND APPARATUS FOR MEASURING ANALYTES

RELATED APPLICATIONS

This application a national stage application under 35 U.S.C. 371 of international application PCT/CA2006/001391, filed Aug. 24, 2006, which claims the priority benefit of U.S. provisional application 60/714,476, filed Sep. 6, 2005. Both of the foregoing applications are hereby incorporated by reference in their entireties.

FIELD OF INVENTION

The present invention relates to a method of measuring the concentration of a compound in a sample on the surface of a part of a subject. The present invention also provides a device for carrying out the method.

BACKGROUND OF THE INVENTION

The concentration of a compound within blood of a subject may be measured using invasive techniques, for example obtaining a blood sample and placing the sample on a device that is introduced into a spectrophotometer. Alternatively, the concentration of the compound may be determined non-invasively by placing a part of the body within a receptor that is coupled to a spectrophotometer, as disclosed in for example, U.S. Pat. No. 5,361,758 (Hall et al.) or U.S. Pat. No. 6,741,876 (Seciena et al.).

Clinical studies have revealed that the concentration of certain compounds in a body part of a subject may be used to assess the risk of development of specific medical conditions in that subject. Early detection of these types of risks in a patient permits measures to be taken that may slow or even prevent the onset of these conditions. As an example, it has been determined that elevated concentration of cholesterol is an indication of a risk for coronary disease. Similarly, the determination of blood glucose levels is required by diabetic patients. Therefore, the development of simple, methods for determining the concentration of a compound is of importance.

In U.S. Pat. No. 6,365,363, Parfenov et al. describe a method of indirectly measuring the concentration of cholesterol in the skin of a subject by enzymatically oxidizing the cholesterol in a section of the subject's skin and then quantitating the amount of the hydrogen peroxide by-product stoichiometrically formed in this reaction using a second enzymatic reaction. As a complex series of enzymatic reactions are used in this method to indirectly determine the concentration of cholesterol, the method is both costly and prone to error. In addition, the development of a result using this method is time consuming.

In U.S. Pat. Nos. 6,236,047 and 6,040,578, Malin et al. describe a method for determining the concentration of a blood compound using light in the near infrared range by analysing diffusively reflecting radiation emerging from the irradiated sample. Hall et al. also describe in U.S. Pat. No. 5,361,758 a non-invasive technique for directly measuring the concentration of constituents of blood using light in the near-infrared range.

Invasive methods for the assay of a compound involve lancing a body part to produce a blood sample and placing anywhere from about 2 to about 250 µl, or more, of the sample within a sample holding device are known, for example a slide well (U.S. Pat. No. 4,387,972, Valencia; U.S. Pat. No. 5,800,781, Gavin et al.; U.S. Pat. No. 5,207,984, Kheiri), a sample tab (e.g. WO 00/70350, Samsoondar) or filter paper strip or the like. The sample holder may then be introduced within a receptor of the sample holding device of a spectrophotometer to determine the concentration of the sample (e.g. WO 98/39634, Samsoondar; WO 99/47261, Samsoondar). This process may be awkward, typically require significant sample volumes, and may require the use of additional devices, for example a capillary tube (e.g. U.S. Pat. No. 4,791,938, Valkenburg) to collect the sample from the body part and transfer the sample to the holding device. Furthermore, as the blood sample is being transferred to a sample holding device, the chance for contamination from an exposed blood sample is present.

SUMMARY OF THE INVENTION

The present invention relates to a method of measuring the concentration of a compound in a sample on the surface of a part of a subject. The present invention also provides a device for carrying out the method.

It is an object of the invention to provide an improved method and apparatus for determining the concentration of an analyte.

According to the present invention there is provided a device for measuring a concentration of one or more than one compound in a sample, comprising:
  a source of electromagnetic radiation (EMR) that emits one or more than one wavelength of EMR, the source of EMR being operatively coupled to a power source;
  a holder for receiving a detachable receptor, the holder comprising one or more than one input in operable association with the source of EMR, one or more than one output in operable association with a detector, the one or more than one input and the one or more than output of the holder in optical alignment with one or more than one port located within the receptor, the one or more than one input and the one or more than output defining an EMR path through the holder and within the receptor, wherein, the sample when received by the receptor is placed within the EMR path;
  the detector for measuring transmitted or reflected EMR received from the sample, the detector operatively coupled to a processing system;
  the processing system comprising one, or more than one calibration algorithm for determining a concentration for the one or more than one compound.

The detachable receptor of the device as described above may be sized to fit over a portion of a body part, sized to fit over a drop of blood located on the body part. Furthermore, the detachable receptor may comprise a matrix that can wick the sample off a surface of a body part. The detachable receptor, or the holder may further comprise an apparatus for lancing a body part when the body part is positioned with the receptor.

The device as described above may further comprise a second path of EMR through the holder and within the detachable receptor, wherein the second path of EMR interacts with the sample at a location separate from that of the EMR path, the second path of EMR is in operative association with the source of EMR or a second source of EMR.

The present invention is also directed to the device as defined above, wherein the holder is a probe, and the probe may be removed from the source of EMR, the detector, or both the source of EMR and detector, but remain in optical association with the source of EMR and the detector.

The present invention also pertains to the device as defined above, wherein the source of EMR comprises wavelengths from about 300 nm to about 2500 nm, or from about 500 nm to about 1100 nm.

The present invention provides a method (A) of determining the concentration of one or more than one compound in a sample of blood comprising,
 (a) placing a receptor over a portion of a body part, the body part having a sample of blood thereon,
 (b) directing a source of electromagnetic radiation (EMR) through the receptor and onto the sample of blood;
 (c) measuring a quantity of the EMR reflected by, or transmitted through, the sample of blood with a detector; and
 (d) performing a quantitative mathematical analysis of the quantity of EMR using an algorithm, and determining the concentration of the one or more than one compound in the sample of blood.

The present invention pertains to the method (A) as defined above, wherein the one or more than one compound may be selected from the group consisting of a fat, a protein, a glycoprotein, hemoglobin, Oxy-Hb, % oxy-Hb, "Oxy-Hb plus Deoxy-Hb", "Total-Hb minus Met-Hb", Met-Hb, % met-Hb, Carboxy-Hb, Co-Hb, Sulf-Hb, $HbA_{1c}$, cholesterol, glucose, a fat, a protein, a glycoprotein, a lipoprotein, a carbohydrate, a steroid, an amino acid, nitrogen, carbon dioxide, cortisol, creatine, creatinine, a ketone, a lipid, urea, a fatty acid, glycosolated hemoglobin, alcohol, lactate, an ion, $Ca^{2+}$, $K^+$, $Cl^-$, $HCO_3^-$, $HPO_4^-$, and a neutral or ionic form of a heavy metal (for example, but not limited to a neutral or ionic form of a metal having an atomic number greater than 20 (calcium), more particularly a metal having an atomic number between 21 (scandium) and 92 (uranium), such as a neutral or ionic form of mercury, arsenic, lead or cadmium).

The present invention embraces the method (A) as described above, wherein prior to the step of placing (step a)), the body part is lanced so that the sample of blood is produced on the surface of the body part. Prior to the step of placing (step (a)), the receptor is placed within a holder, and after the step of measuring (step (c)) the receptor is removed from the holder. Furthermore, the present invention includes the method (A) as defined above, wherein in the step of placing (step (a)), the sample may be wicked within the receptor. The present invention also provides for the method (A) as defined above, wherein the source of EMR comprises wavelengths from about 300 nm to about 2500 nm, or from about 500 nm to about 1100 nm.

The present invention also pertains to the method (A) as defined above, wherein in the step of directing (step (b)), a second source of EMR is directed to the body part, and a measurement of background is obtained. Alternatively, the second source of EMR may be directed to the body part, and in the step of measuring (step (c)), a non-invasive measurement is made of one or more than one compound within the body part, which may be the same as or different from the one or more than one compound measured in the sample of blood.

The present invention also pertains to a method (B) of determining the concentration of one or more than one compound in a sample of blood comprising,
 (a) placing a receptor over a portion of a body part;
 (b) lancing the body part located within the receptor to produce a sample of blood on the surface of the body part,
 (c) directing a source of electromagnetic radiation (EMR) through the receptor and onto the sample of blood;
 (d) measuring a quantity of the EMR reflected by, or transmitted through, the sample of blood with a detector; and
 (e) performing a quantitative mathematical analysis of the quantity of EMR using an algorithm, and determining the concentration of the one or more than one compound in the sample of blood.

The present invention pertains to the method (B) as defined above, wherein the one or more than one compound may be selected from the group consisting of a fat, a protein, a glycoprotein, hemoglobin, Oxy-Hb, % oxy-Hb, "Oxy-Hb plus Deoxy-Hb", "Total-Hb minus Met-Hb", Met-Hb, % met-Hb, Carboxy-Hb, Co-Hb, Sulf-Hb, $HbA_{1c}$, cholesterol, glucose, a fat, a protein, a glycoprotein, a lipoprotein, a carbohydrate, a steroid, an amino acid, nitrogen, carbon dioxide, cortisol, creatine, creatinine, a ketone, a lipid, urea, a fatty acid, glycosolated hemoglobin, alcohol, lactate, an ion, $Ca^{2+}$, $K^+$, $Cl^-$, $HCO_3^-$, $HPO_4^-$ and a neutral or ionic form of a heavy metal (for example, but not limited to a neutral or ionic form of a metal having an atomic number greater than 20 (calcium), more particularly a metal having an atomic number between 21 (scandium) and 92 (uranium), such as a neutral or ionic form of mercury, arsenic, lead or cadmium).

The present invention is directed to the method (B) as defined above, wherein prior to the step of placing (step (a)), the receptor is placed within a holder, and after the step of measuring (step (d)) the receptor is removed from the holder. Furthermore, in the step of placing (step (a)), the sample may be wicked within the receptor.

The present invention also provides for the method (B) as defined above, wherein the source of EMR comprises wavelengths from about 300 nm to about 2500 nm, or from about 500 nm to about 1100 nm.

The present invention also pertains to the method (B) as defined above, wherein in the step of directing (step (c)), a second source of EMR is directed to the body part, and a measurement of background is obtained. Alternatively, the second source of EMR may be directed to the body part, and in the step of measuring (step (d)), a non-invasive measurement is made of one or more than one compound within the body part, which may be the same as or different from the one or more than one compound measured in the sample of blood.

The present invention provides a method (C) of determining the concentration of one or more than one compound in a sample comprising,
 (a) placing a receptor over a portion of a body part, and either
   (i) directing a source of electromagnetic radiation (EMR) through the receptor and the body part;
   (ii) lancing the body part to obtain sample of blood and directing the source of electromagnetic radiation (EMR) through the receptor and the sample of blood;
 or
   (iii) directing the source of electromagnetic radiation (EMR) through the receptor and the body part, and lancing the body part to obtain sample of blood and directing the source of electromagnetic radiation (EMR) through the receptor and the sample of blood;
 (b) measuring a quantity of the EMR reflected by, or transmitted through, the body part, sample of blood, or both the body part and the sample of blood with a detector; and
 (c) performing a quantitative mathematical analysis of the quantity of EMR using an algorithm, and determining the concentration of the one or more than one compound in the body part, the sample of blood, or both the body part and the sample of blood.

The one or more than one compound may be selected from the group consisting of a neutral or ionic form of a heavy metal, for example, a heavy metal having an atomic number greater than 20.

The present invention also pertains the method (C) just defined, wherein prior to the step of directing the EMR on the body part, in steps a) i) or a) iii), the body part is squeezed so that a substantial portion of the blood is removed from the body part to produce a squeezed body part, the EMR is directed onto the squeezed body part, and the one or more than one compound is determined within the squeezed body part.

The present invention also include the method (C) as defined above, wherein in the step of directing the EMR on the body part, in steps a) i) or a) iii), vi) the EMR is directed onto the body part, and the one or more than one compound is determined within the body part the body part to produce a total value of the one or more than one compound, v) the body part is then squeezed so that a substantial portion of the blood is removed from the body part to produce a squeezed body part, the EMR is directed onto the squeezed body part, and the one or more than one compound is determined within the squeezed body part to produce a tissue value of the one or more than one compound; and optionally, vi) determining the blood value of the one or more than one compound by subtracting the tissue value from the total value to obtain the blood value of the one or more than one compound.

Using the device and method of the present invention, the measured concentration of the one or more than one compound may also be correlated to a specific clinical condition or to the propensity for a specific clinical condition.

By determining the concentration of a compound within a sample localized on a surface of a body part, minimal volumes of the sample, for example blood, are required. Furthermore, by placing the receptor of the device directly over the sample, a minimal amount of sample handling is required prior to assay. Providing a receptor that combines the lancing of the body part within the receptor, ensures alignment of the sample within the receptor with the source of EMR, so that the path of EMR interacts with the sample with minimal background effects. Similarly, by providing a receptor that wicks the sample from the surface of the body part and towards the input and output ports of the receptor, ensures that the sample is in optical alignment with the path of EMR and retained within the receptor. The device and methods for obtaining a concentration of a compound within the sample as disclosed herein result in a safe, simple, and efficient method of assaying a compound within a sample. Furthermore, since there is no sample handling, the method and device of the present invention requires the use of a minimal amount of sample for the determination procedure.

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION

Figure 1:
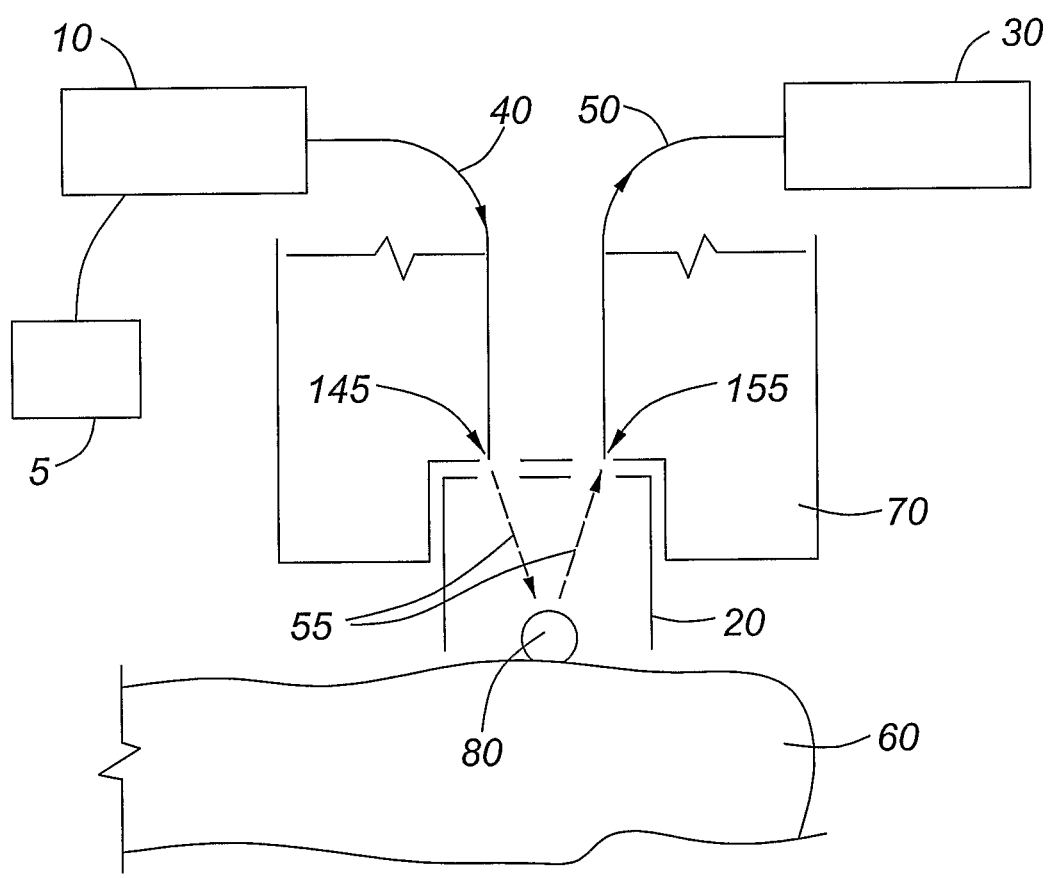
FIG. 1 shows a device (1) in accordance with an embodiment of the present invention placed over a body part (60) with a sample (80) located on the surface pf the body part and within a receptor (20).

The present invention relates to a method of measuring the concentration of a compound in a sample on the surface of a part of a subject. The present invention also provides a device for carrying out the method.

The following description is of a preferred embodiment.

With reference to FIGS. 1-6, the present invention provides a device (1) for measuring a concentration of one or more than one compound in a sample. The device comprises a source of electromagnetic radiation (EMR; 10), a holder (70) for receiving a receptor, the receptor (20), and a detector (30), wherein the source of EMR, the holder, the receptor and the detector are in an operative optical association, so that a path of EMR from the source of EMR, through the holder and receptor to the detector may be established. When a sample (80) is placed within the receptor (20), a parameter of one or more compounds within the sample may be determined.

The source of EMR (10) preferably emits one or more than one wavelength of EMR. For example, which is not to be considered limiting in any manner, the source of EMR may emit one or more than one wavelength of EMR over a range of wavelengths from about 300 nm to about 20,000 nm, or any wavelength therebetween as desired. For example from about 300 nm to about 3,000 nm or any wavelength therebetween, from about 300 nm to about 2,500 nm or any wavelength therebetween, or from about 500 nm to about 2,500 nm or any wavelength therebetween. The source of EMR may be a polychromatic source, an LED source, a laser source, or another source suitable for irradiating a sample at one or more than one desired wavelengths. The source of EMR, and the range of wavelengths emitted by the EMR source is not to be considered limiting in the present invention. The source of EMR is operatively coupled to any suitable power source (5) as would be known to one of skill in the art.

The near infrared region of the electromagnetic spectrum is generally considered to be the spectral interval extending from 650 nm through to 2700 nm and measurements of samples as described herein may be obtained from about 700 nm to about 1100 nm range. Absorption bands observed in this interval are primarily the combination and overtone bands of the fundamental infrared bands. Although very weak in intensity, being typically less than one-tenth in intensity of the fundamental infrared bands, these bands are considered to be analytically useful because nearly all chemical species exhibit characteristic absorption bands in this spectral interval. The near infrared region is particularly well-suited to invasive and non-invasive diagnostic applications because biological samples, or human tissue are somewhat transparent to the incident radiation and therefore sufficient penetration of the radiation is possible to allow accurate quantitative analysis.

The source of EMR used in the present invention to detect the one or more than one compound in the sample or body part is preferably near-infrared light, for example but not limited to a polychromatic light source. This type of light source can emit light over a very wide bandwidth including light in the near infrared spectrum. In this case, the light from the light source preferably passes first through a collimator, which is a collection of lenses that concentrate the light into a narrow parallel beam directed at the receptor. The polychromatic light source can comprise a quartz-halogen or a tungsten-halogen bulb to provide the broad spectrum of light in the near infrared, and is powered by a stabilized power source, for example, a DC power supply, or by a battery. This polychromatic light source may be a tungsten-halogen lamp or it may be a collection of LEDs or other light sources selected to emit radiation in the range of from about 300 nm to about 2,500 nm or any wavelength therebetween, or from about 650 to about 1100 nm. More particularly, the polychromatic light source comprises a source of light that emits a wavelength of light in the visible red spectrum, for example, 660 nm, a wavelength of light in the infrered spectrum, for example, 940 nm, and a broad spectrum of light in the near infrared region.

In a particular non-limiting example, the polychromatic light source may comprise a pair of light emitting diodes that provide light at the wavelengths of 660 nm and 940 nm for detecting the value of oxygen saturation of blood in the part, and a broadband light source that emits a broad spectrum of light in the near infrared. Additional sources of EMR may also be used to determine the concentration of additional compounds with the sample. The light emitting diodes and the broadband light sources may be activated simultaneously, or sequentially so that the concentration of the compound in the sample or body part, and the value of oxygen saturation in the blood are either determined simultaneously, or in a step-wise manner. The one or more than one compound, the oxygen saturation, or a combination thereof may be determined as a concentration value, or as a percentage, for example, a percentage of one compound relative to one or more than one other compound in the sample. In addition, the light emitting diodes may be cycled on and off, many times per second, during the process of acquiring absorbance or transmission data to help eliminate background noise.

The device (1) may be fitted with a holder (70) for receiving a detachable receptor (20). The holder comprises one or more than one radiation guiding elements, for example one or more than one input (40) in operable association with the source of EMR (10), and one or more than one output (50) in operable association with the detector (30). The one or more than one input (40) and the one or more than output (50) of the holder (70) are in an optical alignment with one or more than one port located within the holder (see 145, 155, FIG. 1) and one or more than one port within the receptor (see 140, 150, FIG. 2). The one or more than one input (40) and the one or more than output (50) defining a path of EMR through the holder and within the receptor (e.g. 55), when, the sample (80) is received by the receptor (20) and placed in the path of EMR (55). In the example shown in FIGS. 1 and 2, two ports are shown within the holder and receptor (140, 145, and 150, 155). However, one port may be used (157, FIG. 3), or more than one or two ports may be used, if additional EMR paths are to be used.

The radiation guiding elements (40, 50) may be any suitable element for transmitting radiation, for example but not limited to one or more than one fiber optic bundles, or radiation guiding rods, for example but not limited to fused silica rods. The radiation guiding elements may also be coupled together, so that for example the input path of EMR may pass through an optical fiber oriented circumferentially around a central optical fiber that is used to receive the output EMR, or visa versa. Additional beam-forming elements such as lenses (e.g. 90, 100, FIG. 2) or mirrors may be fitted in the holder and used if desired to ensure that the path of EMR (55) is directed to the sample (80) within the receptor. However, the optical fibers may also be positioned, in the absence of lenses or other path-focusing or directing elements, in a manner that ensures that the path of EMR (55) is directed to the sample (80) within the receptor. If a coupled optical fiber is used (i.e. a fiber carrying both input and output EMR), then one port (157, FIG. 3), or one port and a lens (105), may be used within the holder (70) to input and receive the EMR. The holder may be located within the spectrophotometric device, for example, a hand held device (e.g. see FIG. 4), or located within a holder or probe (70) that is in optical association with the spectrophotometer housing the source of EMR (10) and the detector (30), through optical fibers (40, 50) and the like (see FIG. 5). In this manner, the holder may be in operative association with, and detachable from, the source of EMR, the detector, or both the source of EMR and detector, and may be used, for example, for use with larger spectrophotometric devices.

The receptor (20) may comprise one or more than one input and one or more than one output ports (e.g. 157, FIG. 3, 140, 150, FIG. 2) that are in optical alignment with the input and outputs of the holder (e.g. 105, FIG. 3, 145, 155, FIG. 1) to permit entry of EMR (55) from the holder (70) to the receptor (20), and its return to the holder following interaction of the EMR with the sample (80).

The receptor (20) matingly engages with the holder (70) and can easily be removed from the holder after use. The receptor may be in press fit engagement with the holder, snap into place, be retained via any suitable biasing means, for example a spring, and the like. If desired, a tab may be added to the receptor to facilitate installation and removal of the receptor from the holder.

Figure 2:
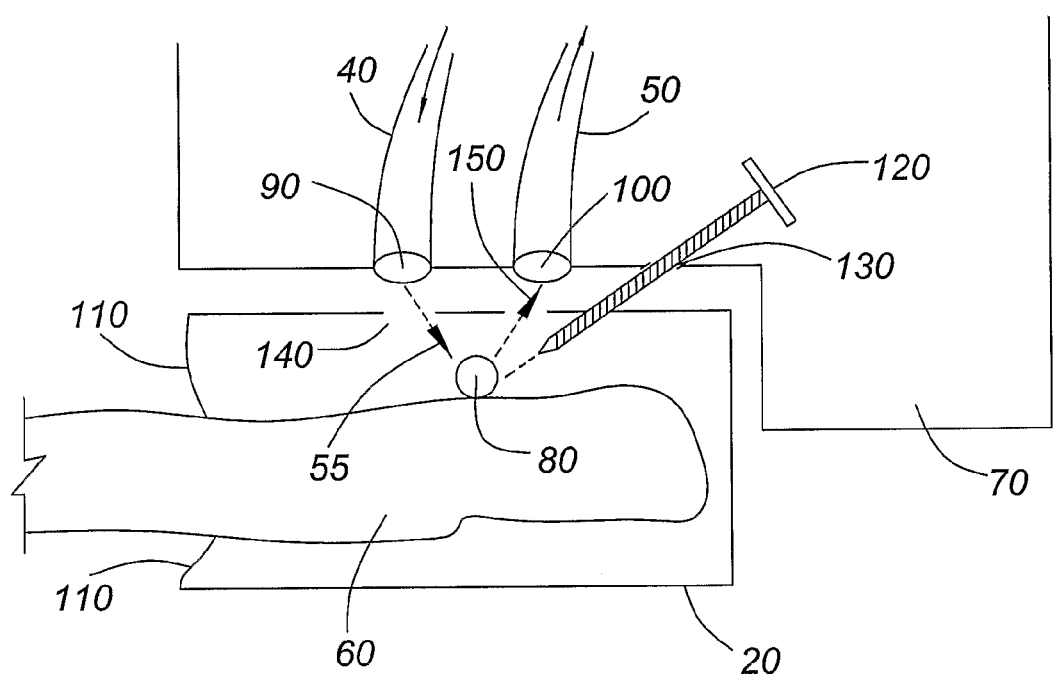
FIG. 2 shows a receptor (20) and holder (70) in accordance with a further embodiment of the present invention.
Figure 3:
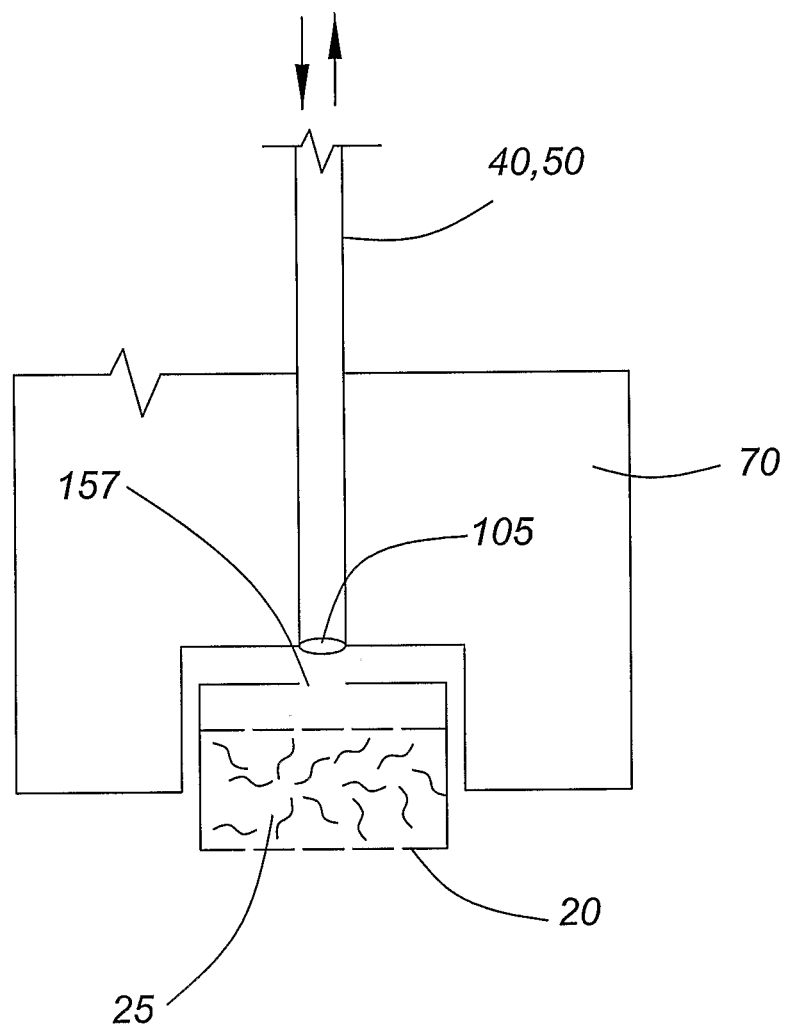
FIG. 3 shows a receptor (20) and holder (70) in accordance with a further embodiment of the present invention comprising a wicking material (25).
Figure 4:
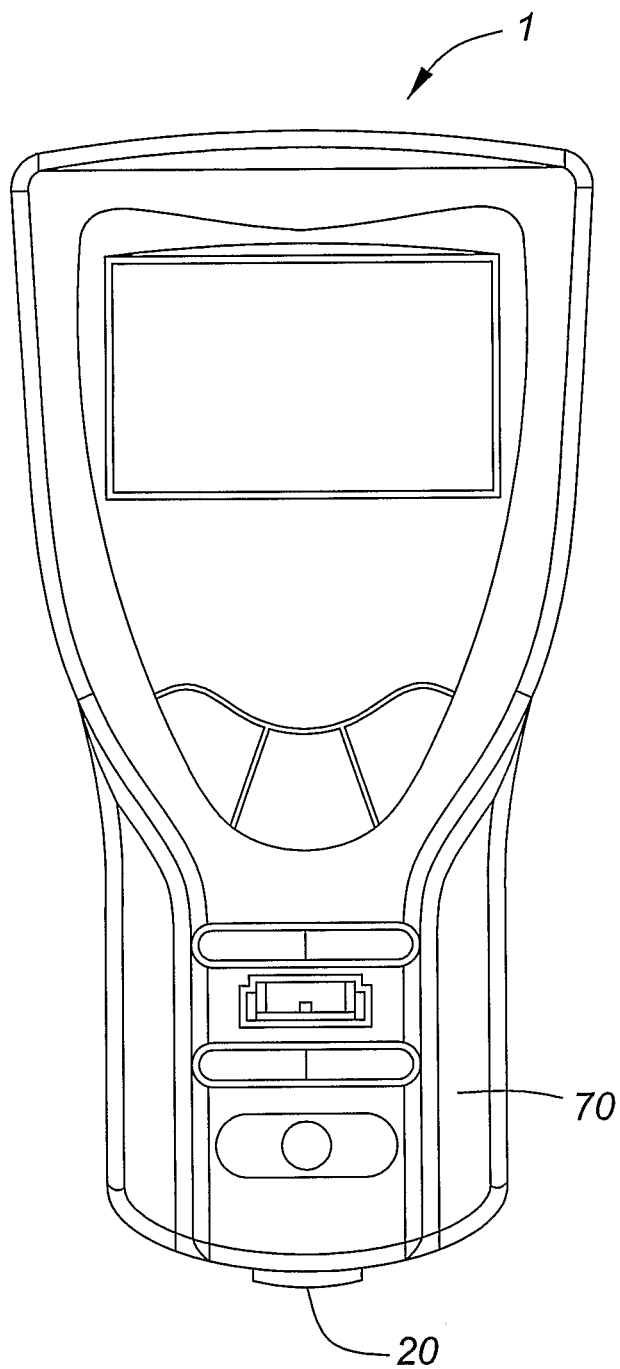
FIG. 4 shows a hand-held device in accordance with a further embodiment of the present invention.
Figure 5:
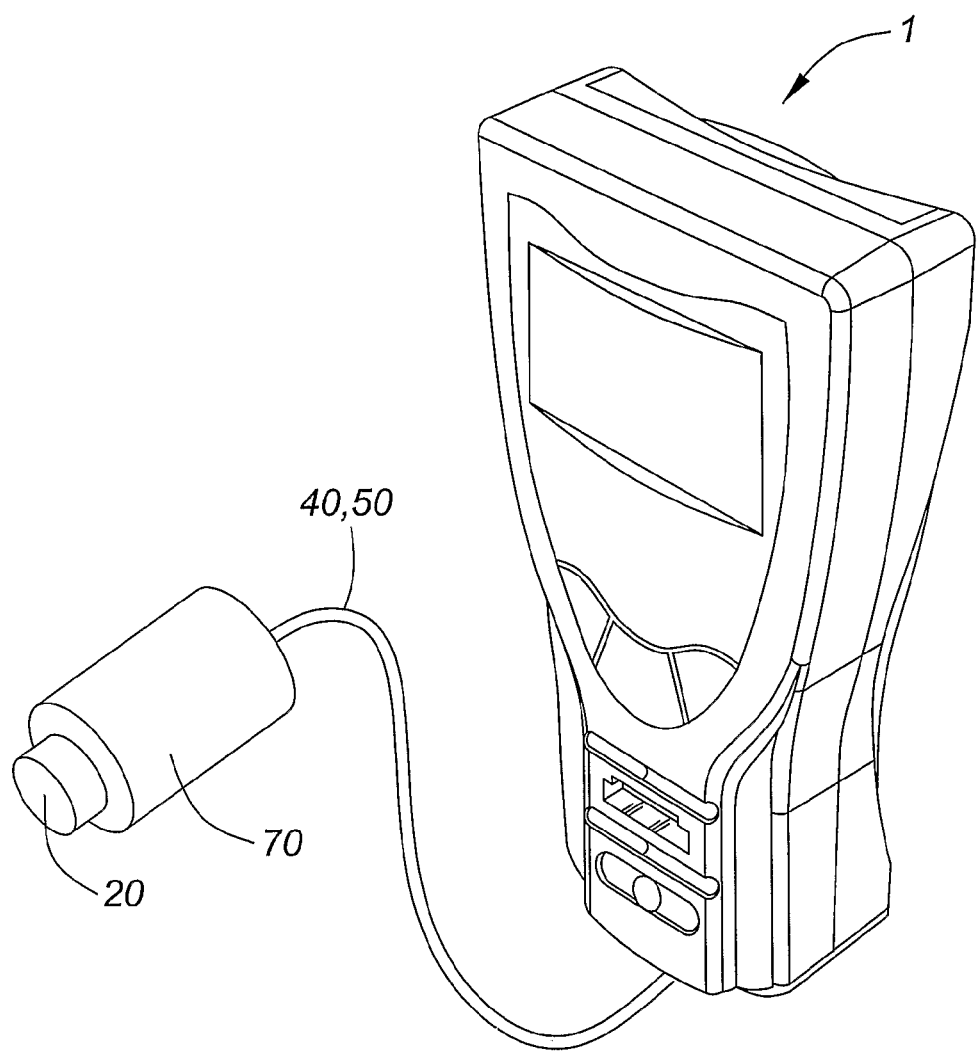
FIG. 5 shows a hand held device with a detachable probe in accordance with a further embodiment of the present invention.

The receptor (20) may be sized to fit over the sample (80) located on the surface of a body part (60) as shown in FIG. 1, or it may be sized to receive the body part (60), and sample (80) as shown in FIG. 2. Preferably, the placement of the receptor over the body part ensures removal of a substantial amount of stray ambient light during the measurement. If the receptor fits over the body part as shown in FIG. 2, then a light shield (110, FIG. 2) may be used that fits around the body part when it is placed in the receptor.

The receptor may be made from a material that can be discarded after use to minimize contamination from the sample.

The receptor may also comprise a material (25, FIG. 3) that wicks the sample away from the skin surface, towards the input and output ports of the receptor, and into the path of the EMR within the receptor. For example, which is not to be considered limiting in ay any manner, the sample may be immobilized within the receptor by absorption or capillary action, within filter paper, glass wool, one or more than one capillary tubes made from polymeric or other rigid or semi rigid material, or any other material known to wick a liquid sample. Preferably, the material used is transparent to the wavelength of light used in the device. The immobilized sample within the receptor is then irradiated with EMR in order to assay one or more than one compound with the sample. With this arrangement, the sample is immobilized and retained within the receptor. By removing the sample from the body part, this also ensures minimal contamination from the sample, during use. After the sample is immobilized within the receptor, a measurement of one or more than one compound may be obtained as described above, or the device, or probe holding the receptor may be removed from the body part and the measurement obtained. If required, an opaque cover may be fitted over the receptor to block ambient light during the measurement of the sample. After the measurement is taken, the receptor may then be removed and discarded from the holder of the device or probe.

In an alternative embodiment of the present invention, the receptor may also comprise a device for lancing the body part (120, FIG. 2). In this embodiment, the body part is placed under or within the receptor, and the device for lancing the body part is used to prick or lance the skin in order to produce a sample (80). The lancing device may targeted to a location on the body part via a guide (130). In this manner, if required, the sample produce as a result of the lancing device is positioned within the path of the EMR within the receptor (FIG. 2).

If a total analysis of one or more than one compound in a body part is desired, the receptor may be placed, or pressed, against the skin of the body part and used to determine the concentration of the one or more than one compound within all of the compartments of the body part, for example, but not limited to the vascular, interstitial, cellular, lymph, bone and connective tissue compartments. However, it may be desired that the blood content of the skin within the sample area be reduced, for example, if the concentration of a compound in non-blood compartments or within a tissue is to be determined. If reduced blood content of the skin is desired, the skin may be lightly pressed in any suitable manner, for example, a portion of skin may be clamped or pressed by the receptor, as described, for example, in U.S. Patent Application Publication No. 2004/0015060, published on Jan. 22, 2004, the disclosure of which is incorporated by reference herein. Alternatively, the blood and/or fluid within an area of the body part to be measured may be removed through the use of O-rings, rollers, an inflatable pneumatic cuff, or a mechanical piston disposed within the receptor, or a positive pressure/vacuum system connected to the receptor, or a combination thereof, as described by U.S. patent application Ser. No. 10/745,234, filed Dec. 22, 2003, the disclosure of which is incorporated by reference herein.

Therefore, the present invention also provides a method of determining the concentration of one or more than one compound in a sample comprising, (a) placing a receptor over a portion of a body part, and either
  (i) directing a source of electromagnetic radiation (EMR) through the receptor and the body part;
  (ii) lancing the body part to obtain sample of blood and directing the source of electromagnetic radiation (EMR) through the receptor and the sample of blood;
  or
  (iii) directing the source of electromagnetic radiation (EMR) through the receptor and the body part, and lancing the body part to obtain sample of blood and directing the source of electromagnetic radiation (EMR) through the receptor and the sample of blood (b) measuring a quantity of the EMR reflected by, or transmitted through, the body part, sample of blood, or both the body part and the sample of blood with a detector; and (c) performing a quantitative mathematical analysis of the quantity of EMR using an algorithm, and determining the concentration of the one or more than one compound in the body part, the sample of blood, or both the body part and the sample of blood.

Furthermore, in the step of directing the EMR on the body part (steps a) i) or a) iii)), the method may additionally comprise the following steps:

1) the EMR is directed onto the body part, and the one or more than one compound is determined within the body part to produce a total value of the one or more than one compound, 2) the body part is then squeezed so that a substantial portion of the blood is removed from the body part to produce a squeezed body part, the EMR is directed onto the squeezed body part, and the one or more than one compound is determined within the squeezed body part to produce a tissue value of the one or more than one compound; and if desired, 3) determining the blood value of the one or more than one compound by subtracting the tissue value from the total value to obtain the blood value of the one or more than one compound.

The one or more than one compound may for example, which is not to be considered limiting in any manner, be selected from the group consisting of a neutral or ionic form of a heavy metal having an atomic number greater than 20, or a metal having an atomic number between 21 (scandium) and 92 (uranium), such as a neutral or ionic form of mercury, arsenic, lead or cadmium.

In another alternative embodiment, the holder (70) may also receive a suitable sized sample holder, for example a slide well (U.S. Pat. No. 4,387,972, Valencia; U.S. Pat. No. 5,800,781, Gavin et al.; U.S. Pat. No. 5,207,984, Kheiri), a sample tab (e.g. WO 00/70350, Samsoondar), a filter paper strip or the like. The sample holder may be introduced within the holder (70) of the device of the present invention to determine the concentration of the sample. In this embodiment, the lid of the sample tab, or slide well is transparent or comprises transparent portions to permit the entry and exit of EMR to interact with the sample.

The reflected, transmitted, or both, EMR following interaction with the sample is collected by using any suitable method, for example, fiber optics, or one or more lenses (e.g. 90, 100), and the output signal (50) directed to a diffraction device that separates the wavelengths of light within the output signal into their component parts. Examples of a diffraction device include but are not limited to a diffraction grating or a holographic grating. The diffracting device preferably disperses the EMR into its component wavelengths so that the dispersed EMR falls along the length of a detector such as, but not limited to a linear array detector (e.g. a 256 element photo diode array), or a CCD. In the case of an array, the detector has a series of diodes and is preferably electronically scanned by a microprocessor to measure the charge accumulated on each diode, the charge being proportional to the intensity of EMR for each wavelength transmitted through or reflected from the part of the subject in the receptor.

The detector is connected to the microprocessor, producing an output spectrum, with the microprocessor analyzing the measurements and ultimately producing a result for each concentration level determined. The processing may comprise one or more than one calibration algorithm (for example as disclosed in U.S. Pat. No. 6,651,015, Samsoondar, which is incorporated herein by reference) that is used to determine a property of one or more than one compound within the sample (80). The result can be stored, shown on a display, or printed on a printer. A keyboard may also be used to allow a user to control the device, for example, to specify a particular constituent to be measured. The timing and control may be activated by a microprocessor to control the device, for example, to determine number and timing of measurements.

If required, the device (1) may also have a second path of EMR (57, FIG. 6) comprising an input (45) and output (47) path that enters the receptor. The second path of EMR interacts with the body part (60) at a location (85) separate from that of the path of EMR that interacts with the sample (80). The second path of EMR (57) is also in operative association with the source of EMR (10), or it may be in operative association with a second source of EMR. The second path of EMR may be used to control for background signals within the receptor (20) and body part (60), or it may be used to determine the concentration of a compound within the body part in a non-invasive manner, for example as described in U.S. Pat. No. 5,361,758 (Hall) or U.S. Pat. No. 6,741,876 (Seciena et al., both of which are incorporated herein by reference).

Therefore, the present invention provides a device for measuring a concentration of one or more than one compound in a sample, comprising:

a source of electromagnetic radiation (EMR) that emits one or more than one wavelength of EMR, the source of EMR being operatively coupled to a power source;

a holder for receiving a detachable receptor, the holder comprising one or more than one input in operable association with the source of EMR, one or more than one output in operable association with a detector, the one or more than one input and the one or more than output of the holder in optical alignment with one or more than one port located within the receptor, the one or more than one input and the one or more than output defining an EMR path through the holder and within the receptor, wherein, the sample when received by the receptor is placed within the EMR path;

the detector for measuring transmitted or reflected EMR received from the sample, the detector operatively coupled to a processing system;

the processing system comprising one, or more than one calibration algorithm for determining a concentration for the one or more than one compound.

The device of the present invention may be used to determine the concentration of one or more than one compound, or a percentage of a compound with reference to another compound (i.e. the relative abundance of one compound with respect to another compound) within the sample. The compound may be any compound, and the invention is not meant to be limited by the compound, or compounds, being assayed. For example, which is not to be considered limiting, if the sample is a biological fluid, the compound may be selected from the group consisting of a fat, a protein, a glycoprotein, hemoglobin, Oxy-Hb, % oxy-Hb, "Oxy-Hb plus Deoxy-Hb", "Total-Hb minus Met-Hb", Met-Hb, % met-Hb, Carboxy-Hb, Co-Hb, Sulf-Hb, $HbA_{1c}$, cholesterol, glucose, a fat, a protein, a glycoprotein, a lipoprotein, a carbohydrate, a steroid, an amino acid, nitrogen, carbon dioxide, cortisol, creatine, creatinine, a ketone, a lipid, urea, a fatty acid, glycosolated hemoglobin, alcohol, lactate, an ion, $Ca^{2+}$, $K^+$, $Cl^-$, $HCO_3^-$, $HPO_4^-$ and a neutral or ionic form of a heavy metal, or a toxic metal, for example, but not limited to a neutral or ionic form of a metal having an atomic number greater than 20 (calcium), more particularly a metal having an atomic number between 21 (scandium) and 92 (uranium), such as a neutral or ionic form of mercury, arsenic, lead or cadmium.

The processing system of the device of the present invention may be used to determine the oxygen saturation of blood in the part by analyzing the differential absorption of oxygenated hemoglobin, $HbO_2$, and deoxygenated hemoglobin, Hb in arterial blood. Based on the absorbances of the wavelengths of light in the visible red and infrared spectra, the system can calculate a value of arterial oxygen saturation ($SP_aO_2$) of hemoglobin in the blood of the subject. The system can distinguish hemoglobin absorption from absorption of other components of the tissues within the part based upon the pulsatile nature of arterial blood. In this embodiment, the processing system may further comprise a pulse oximeter.

The concentration of a given compound is preferably calculated according to the present invention by using a calibration equation derived from a statistical analysis, for example but not limited to a least squares best fit, of a plot of the values of concentration of a calibration set of samples of the compound, which are determined using known methods (e.g. U.S. Pat. No. 6,651,015, Samsoondar). However, it is to be understood that other statistical tests may be used was known in the art, for example but not limited to multiple linear regression (MLR), partial least squares (PLS), and the like. Any known method for determining the concentration of one, or more than one, compound may be used as would be known to one of skill in the art.

Figure 6:
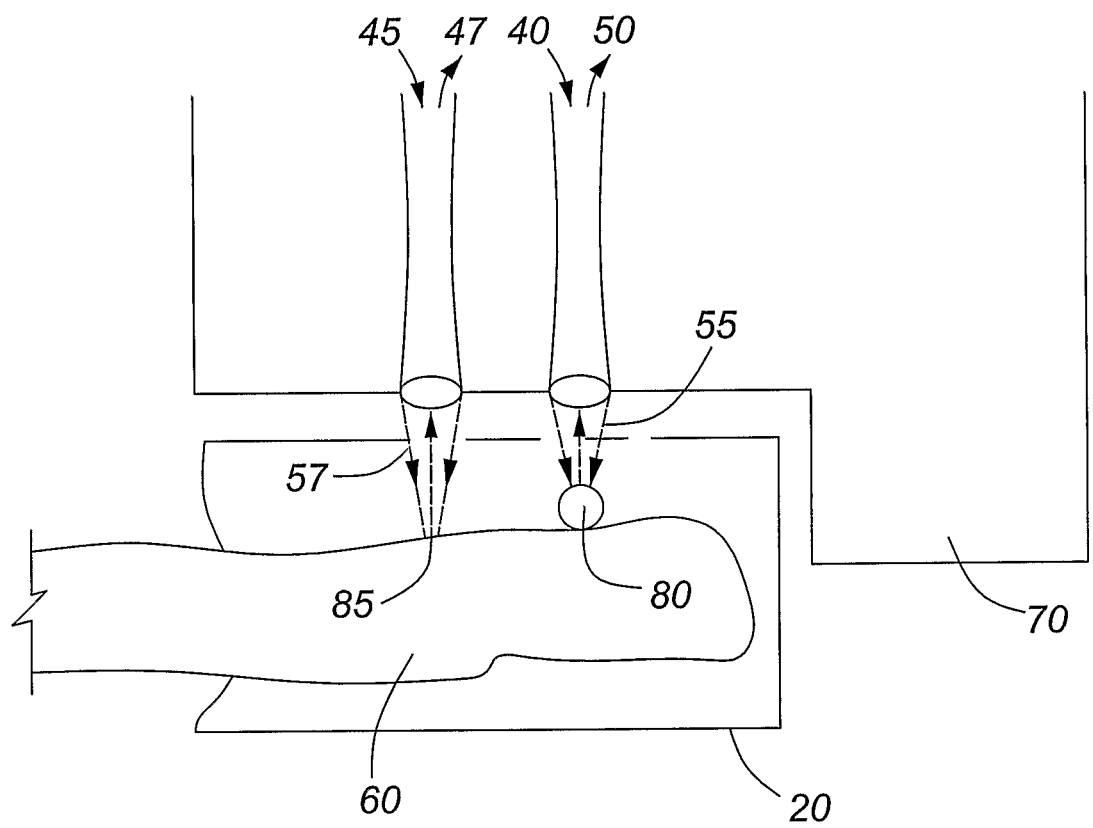
FIG. 6 shows a receptor (20) and holder (70) in accordance with a further embodiment of the present invention.

The present invention also provides a method to determine the concentration of one or more than one compound within the sample and a similar or different compound within the body part that lies along the paths of EMR emitted, and received by, the receptor. In this example, there are two sources of EMR traveling within two paths of EMR. One path of EMR interacts with the sample, for example a drop of blood, while the second path of EMR may interact with the body part in a non-invasive manner, as shown in FIG. 6.

The present invention also provides for a method of determining the concentration of a compound in a sample of blood comprising, (a) placing a receptor over a portion of a body part, the body part having a sample thereon, the sample may be blood;

(b) directing a source of electromagnetic radiation (EMR) through the receptor and onto the sample;

(c) measuring a quantity of the EMR reflected by, or transmitted through, the sample with a detector; and (d) performing a quantitative mathematical analysis of the quantity of EMR using an algorithm, and determining the concentration of the compound in the sample.

Prior to the step of placing (step a)), the body part may be pricked or lanced so that the sample is a sample of blood, and the blood is produced on the surface of the body part.

Furthermore, the present invention provides a method of determining the concentration of a compound in a sample of blood comprising, (a) placing a receptor over a portion of a body part;

(b) lancing the body part located within the receptor to produce a sample of blood on the surface of the body part, (b) directing a source of electromagnetic radiation (EMR) through the receptor and onto the sample of blood;

(c) measuring a quantity of the EMR reflected by, or transmitted through, the sample of blood with a detector; and (d) performing a quantitative mathematical analysis of the quantity of EMR using an algorithm, and determining the concentration of the compound in the sample of blood.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A method of determining the concentration of one or more than one compound in a sample comprising, (a) placing a receptor over a portion of a body part, and either (i) directing a source of electromagnetic radiation (EMR) through the receptor and the body part; (ii) lancing the body part to obtain sample of blood and directing the source of electromagnetic radiation (EMR) through the receptor and the sample of blood; or (iii) directing the source of electromagnetic radiation (EMR) through the receptor and the body part, and lancing the body part to obtain sample of blood and directing the source of electromagnetic radiation (EMR) through the receptor and the sample of blood;

(b) measuring a quantity of the EMR reflected by, or transmitted through, the body part, sample of blood, or both the body part and the sample of blood with a detector; and (c) performing a quantitative mathematical analysis of the quantity of EMR using an algorithm, and determining the concentration of the one or more than one compound in the body part, the sample of blood, or both the body part and the sample of blood, wherein the one or more than one compound may be selected from the group consisting of a neutral or ionic form of a heavy metal having an atomic number greater than 20, wherein prior to the step of directing the EMR on the body part, in steps a) i) or a) iii), the body part is squeezed so that a substantial portion of the blood is removed from the body part to produce a squeezed body part, the EMR is directed onto the squeezed body part, and the one or more than one compound is determined within the squeezed body part.

2. The method claim 1, wherein prior to the step of placing (step (a)), the receptor is placed within a holder.

3. The method of claim 1, wherein after the step of measuring (step (b)) the receptor is removed from the holder.

4. The method according to claim 1, wherein in the step of directing (step (a)), the source of EMR comprises wavelengths from about 300 nm to about 2500 nm.

5. The method according to claim 1, wherein in the step of directing (step (a)), the source of EMR comprises wavelengths from about 500 nm to about 1100 nm.

6. The method of claim 1, wherein in the step of directing (step (a)), a second source of EMR is directed to the body part, and a measurement of background is obtained.

7. A method of determining the concentration of one or more than one compound in a sample comprising, (a) placing a receptor over a portion of a body part, and either (i) directing a source of electromagnetic radiation (EMR) through the receptor and the body part; (ii) lancing the body part to obtain sample of blood and directing the source of electromagnetic radiation (EMR) through the receptor and the sample of blood; or (iii) directing the source of electromagnetic radiation (EMR) through the receptor and the body part, and lancing the body part to obtain sample of blood and directing the source of electromagnetic radiation (EMR) through the receptor and the sample of blood;

(b) measuring a quantity of the EMR reflected by, or transmitted through, the body part, sample of blood, or both the body part and the sample of blood with a detector; and (c) performing a quantitative mathematical analysis of the quantity of EMR using an algorithm, and determining the concentration of the one or more than one compound in the body part, the sample of blood, or both the body part and the sample of blood, wherein the one or more than one compound may be selected from the group consisting of a neutral or ionic form of a heavy metal having an atomic number greater than 20, wherein in the step of directing the EMR on the body part, in steps a) i) or a) iii), 1) the EMR is directed onto the body part, and the one or more than one compound is determined within the body part to produce a total value of the one or more than one compound, 2) the body part is then squeezed so that a substantial portion of the blood is removed from the body part to produce a squeezed body part, the EMR is directed onto the squeezed body part, and the one or more than one compound is determined within the squeezed body part to produce a tissue value of the one or more than one compound; and optionally, 3) determining the blood value of the one or more than one compound by subtracting the tissue value from the total value to obtain the blood value of the one or more than one compound.

8. The method claim 7, wherein prior to the step of placing (step (a)), the receptor is placed within a holder.

9. The method of claim 7, wherein after the step of measuring (step (b)) the receptor is removed from the holder.

10. The method according to claim 7, wherein in the step of directing (step (a)), the source of EMR comprises wavelengths from about 300 nm to about 2500 nm.

11. The method according to claim 7, wherein in the step of directing (step (a)), the source of EMR comprises wavelengths from about 500 nm to about 1100 nm.

12. The method of claim 7, wherein in the step of directing (step (a)), a second source of EMR is directed to the body part, and a measurement of background is obtained.

* * * * *